(12) United States Patent
Kang et al.

(10) Patent No.: US 10,973,808 B2
(45) Date of Patent: Apr. 13, 2021

(54) BOWEL CLEANSING COMPOSITION (71) Applicants: Yoon Sik Kang, Seoul (KR); Chung Yoon Shin, Seoul (KR); Hyun Suk Kang, Seoul (KR); Hyun Yee Kang, Seoul (KR)

(72) Inventors: Yoon Sik Kang, Seoul (KR); Chung Yoon Shin, Seoul (KR); Hyun Suk Kang, Seoul (KR); Hyun Yee Kang, Seoul (KR)

( * ) Notice: Subject to any disclaimer, the term of this patent is extended or adjusted under 35 U.S.C. 154(b) by 0 days.

(21) Appl. No.: 15/843,070

(22) Filed: Dec. 15, 2017

(65) Prior Publication Data

US 2018/0104225 A1 Apr. 19, 2018

Related U.S. Application Data (63) Continuation of application No. 14/903,779, filed as application No. PCT/KR2014/008893 on Sep. 24, 2014, now abandoned.

(30) Foreign Application Priority Data

Oct. 17, 2013 (KR) .................. 10-2013-0124072
Jun. 30, 2014 (KR) .................. 10-2014-0081087

(51) Int. Cl.
*A61K 31/4402* (2006.01)
*A61K 45/06* (2006.01)
*A23L 2/52* (2006.01)
*A61K 9/00* (2006.01)
*A61K 31/375* (2006.01)
*A61K 31/047* (2006.01)

(52) U.S. Cl.
CPC ............ *A61K 31/4402* (2013.01); *A23L 2/52* (2013.01); *A61K 9/0095* (2013.01); *A61K 31/047* (2013.01); *A61K 31/375* (2013.01); *A61K 45/06* (2013.01); *A23V 2002/00* (2013.01)

(58) Field of Classification Search
CPC ............ A61K 31/4402; A61K 9/0095; A61K 31/047; A61K 31/475; A61K 45/06; A23L 2/52; A23V 2002/00

See application file for complete search history.

(56) References Cited

U.S. PATENT DOCUMENTS

| | | |
|---|---|---|
| 3,211,614 A | 10/1965 | Embring et al. |
| 5,274,001 A | 12/1993 | Borody |
| 7,169,381 B2 | 1/2007 | Barras et al. |
| 2006/0034939 A1 | 2/2006 | Kunogi et al. |
| 2006/0251749 A1 | 11/2006 | Jia et al. |
| 2009/0324736 A1 | 12/2009 | Johnson et al. |
| 2010/0297264 A1 | 11/2010 | Kastenberg |
| 2012/0195980 A1 | 8/2012 | Shaver |
| 2013/0136806 A1 | 5/2013 | Zanarotti et al. |
| 2013/0295018 A1 | 11/2013 | Motoyama et al. |

FOREIGN PATENT DOCUMENTS

| | | | |
|---|---|---|---|
| AU | 8905659 A1 | 6/1989 | |
| CN | 1868486 A | 11/2006 | |
| CN | 101217968 A | 7/2008 | |
| CN | 103237563 A | 8/2013 | |
| EP | 2322190 A1 | 5/2011 | |
| EP | 2 626 085 A1 | 8/2013 | |
| EP | 2626085 A1 * | 8/2013 | ......... A61K 49/0452 |
| EP | 2626085 A1 | 8/2013 | |
| JP | 59-080608 | 5/1984 | |
| JP | 59-112918 | 6/1984 | |
| JP | 03-284620 | 12/1991 | |
| JP | 05-255092 | 10/1993 | |
| JP | H-08-505609 A | 6/1996 | |
| JP | 2011500711 A | 1/2011 | |
| JP | 2011-519952 A | 7/2011 | |
| KR | 1020060095081 | 10/2006 | |
| WO | 89/05659 A1 | 6/1989 | |
| WO | WO-8905659 A1 * | 6/1989 | ........... A61K 31/375 |
| WO | 2004052338 A1 | 6/2004 | |

(Continued)

OTHER PUBLICATIONS

Akaike N et al., entitled "In Vitro Study on the Bowel Cleansing Preparation AJG522 for Explosive Gas Production by Intestinal Bacteria Using Dog Feces," J. New. Rem. & Clin., vol. 62, No. 6, 2013, 8 pages, English Abstract.

PCT International Search Report dated Dec. 30, 2014 in connection with PCT International Patent Application No. PCT/KR2014/008893, 1 page.

Lee, J W et al., entitled "Comparison between Conventional 4 L Polyethylene Glycol and Combination of 2 L Polyethylene Glycol and Sodium Phosphate Solution as Colonoscopy Preparation," Korean J Gastroenterol, Nov. 2010;56(5):299-306.

Ladas, S D et al., entitled "Colonic gas explosion during therapeutic colonoscopy with electrocautery," World J Gastroenterol, Oct. 28, 2007; 13(40): 5295-5298.

Nunes, BLBBP et al., entitled "Comparative Evaluation of Bowel Preparation for Colonoscopy Using Mannitol and Polyethylene Glycol—A Prospective Study," Rev bras. colo-proctol. [online], 2008, vol. 28, No. 3, pp. 294-298. English Abstract.

(Continued)

*Primary Examiner* — Jeffrey S Lundgren
*Assistant Examiner* — Ibrahim D Bori
(74) *Attorney, Agent, or Firm* — Amster, Rothstein & Ebenstein LLP (57) ABSTRACT

A bowel cleansing composition includes as a first cleansing ingredient, a specific sugar alcohol such as xylitol, sorbitol, etc., as a second cleansing ingredient glycerol, erythritol, threitol, arabitol, ribitol, mannitol, galactitol, fucitol, iditol, inositol, volemitol, isomalt, maltitol, lactitol, maltotriitol, maltotetraitol, and polyglycitol, as a second cleansing ingredient ascorbic acid or a mixture of ascorbic acid and a salt of ascorbic acid, as a third cleansing ingredient picosulfate, and an aqueous solvent, wherein the concentration of the first cleansing ingredient is 10 g/L to 500 g/L based on the total composition, the concentration of the second cleansing ingredient is 15 g/L to 500 g/L based on the total composition, the concentration of the third cleansing ingredient is 1 mg/L to 100 mg/L based on the total composition, and the volume of the aqueous solvent is 0.1 L to 1.0 L.

14 Claims, 5 Drawing Sheets

(56) References Cited

FOREIGN PATENT DOCUMENTS

| WO | 2011027363 A2 | 3/2011 |
|---|---|---|
| WO | 2012079118 A1 | 6/2012 |
| WO | 2012102799 A2 | 8/2012 |
| WO | 2012123720 A1 | 9/2012 |

OTHER PUBLICATIONS

Communication for the ASGE Technology Committee entitled "Colonoscopy Preparation," Technology Status Evaluation Report, American Society for Gastrointestinal Endoscopy, vol. 69, No. 7, 2009, pp. 1201-1209.

National Cancer Institute, entitled "High-Dose Vitamin C-for health professionals (PDQ®)," updated Jun. 29, 2015 at http://www.cancer.gov/about-cancer/treatment/cam/hp/vitamin-c-pdq, 10 pages.

Padayatty, S J et al., entitled "Vitamin C Pharmacokinetics: Implications for Oral and Intravenous Use," Annals of Internal Medicine, Apr. 6, 2004, vol. 140, No. 7, pp. 533-538.

Hoffer, L J et al., entitled "Phase I clinical trial of i.v. ascorbic acid in advanced malignancy," Annals of Oncology 19; 1969-1974, 2008.

Welsh, J L et al., entitled "Pharmacological Ascorbate with Gemcitabine for the Control of Metastatic and Node-Positive Pancreatic Cancer (PACMAN): Results from a Phase I Clinical Trial," Cancer Chemother Pharmacol., Mar. 2013; 71(3): 765-775.

Wexner, S D et al., entitled "A consensus document on bowel preparation before colonoscopy: Prepared by a Task Force From The American Society of Colon and Rectal Surgeons (ASCRS), the American Society for Gastrointestinal Endoscopy (ASGE), and the Society of American Gastrointestinal and Endoscopic Surgeons (SAGES)," Gastrointestinal Endoscopy, vol. 63, No. 7, Jun. 2006, 894-909.

Minervini S et al., entitled "Comparison of Three Methods of Whole Bowel Irrigation" Am J Surg, Sep. 1980;140 (3):400-2.

Donovan I A et al., entitled "Modification of the physiological disturbances produced by whole gut irrigation by preliminary mannitol administration," BR. J. Surg., vol. 67 (1980) 138-139.

Akaike N et al., entitled "In Vitro Study on the Bowel Cleansing Preparation AJG522 for Explosive Gas Production by Intestinal Bacteria Using Dog Feces," J. New Rem. & Clin., vol. 62, No. 6, 2013, 8 pages with English Abstract Only.

Korsten M A et al., entitled "A Prospective Assessment of Renal Impairment After Preparation for Colonoscopy: Oral Sodium Phosphate Appears to Be Safe in Well-Hydrated Subjects with Normal Renal Status," Dig Dis Sci (2010) 55:2021-2029.

Communication Supplementary European Search Report dated Oct. 7, 2015 in connection with European Patent Application No. 14853287.2, 3 pages.

Communication Supplementary European Search Report dated Apr. 13, 2016 in connection with European Patent Application No. 14854467.9, 6 pages.

Hyperosmotic Laxatives, retrieved from the Internet on Jun. 5, 2017 at https:www.drugs.com/monograph/hyperosmotic-laxatives.html, 12 pages.

Japanese Office Action, dated Nov. 6, 2018, in connection with Japanese Patent Application No. 2016-548986.

\* cited by examiner

Fig. 1

Unit: $10^5$ CFU/ml

Fig. 2

| Lab: Green Cross | Specimen 1 | Specimen 2 | Specimen 3 | Specimen 4 | Specimen 5 | Average |
|---|---|---|---|---|---|---|
| Ex. 1 | 0.02 | 0.7 | 2 | No growth | 70 | 14.5 |
| Ref Ex. 1 (PICOLYTE) | 70 | 580 | 500 | 1 | 360 | 302.2 |
| Control (bottled water) | 42 | 30 | 23 | 0.7 | 70 | 33.1 |

Unit: $10^5$ CFU/ml

BOWEL CLEANSING COMPOSITION

CROSS-REFERENCE TO RELATED APPLICATIONS

This application is a continuation of U.S. patent application Ser. No. 14/903,779, filed Jan. 8, 2016, which is a U.S. national phase of PCT Application No. PCT/KR2014/008893, filed Sep. 24, 2014, which claims priority to Korean Application No. 10-2013-0124072, filed Oct. 17, 2013 and Korean Application No. 10-2014-0081087, filed Jun. 30, 2014, the contents of each of which are incorporated by reference herein.

FIELD OF THE INVENTION

The present invention relates to a bowel cleansing composition. More specifically, the present invention relates to a novel bowel cleansing composition comprising high concentrations of a specific sugar alcohol and ascorbic acid in addition to picosulfate that is a laxative agent so as to improve the ease of administration by reducing the total dosage and yet improve bowel cleansing efficacy while ensuring safety.

BACKGROUND OF THE INVENTION

According to the reports from the World Cancer Research Fund International, colon cancer is the third most common cancer worldwide with incidences of colon cancer during the year 2012 estimated to be 1.4 million worldwide and expected to be 2.4 million in the year 2035. For the diagnosis of colon cancer, colonoscopy is essential. Moreover, colonoscopy is very important because colon cancer can be prevented if colon polyps, which are considered to be the precursor of colon cancer, are detected during colonoscopy and removed.

For accurate colonoscopy examination, bowel cleansing prior to the procedure is essential; since stool may be retained inside the colon even after fasting for days, it is necessary to cleanse the colon thoroughly by artificial methods prior to the examination. For this purpose, methods have been developed where cleansing liquids comprised of laxative agents are ingested to empty the colon. An ideal bowel cleansing agent should have high cleansing power, ease of administration, as well as safety.

Firstly, high cleansing power is an essential requirement for an accurate colonoscopy procedure. If too much residue remains after bowel cleansing, it is difficult to perform an accurate examination, and the poor visualization increases the risk of complications such as perforation, and sometimes the painful bowel procedure has to be repeated, which might result in the patient's refusal or avoidance of the examination. Thus, reliable cleansing efficacy is the most important requirement.

Secondly, the ease of administration is determined by the volume of the bowel cleansing agent to be ingested, the taste of the agent, and the occurrence of discomforts such as nausea, vomiting, and abdominal pain following the ingestion of the agent. Even if a bowel cleansing agent has excellent cleansing power, if its administration is difficult, one cannot successfully complete the intake process in accordance with the dosing regimen, resulting in inadequate bowel cleansing. In addition, the unpleasant experience with bowel cleansing often leads to the refusal of repeat examination, and rumors about the difficulties of administration may impede the popularization of colonoscopies harming public health.

Thirdly, as a safety requirement, bowel cleansing should minimize temporary disorders and should not cause irreversible chronic disorders.

Early regimens involved ingesting a large volume of up to 7-12 L of solutions like saline solutions as bowel cleansing agents. However, administration of such cleansing preparations was accompanied by a great deal of pain and difficulties.

Later, bowel cleansing preparations using 2 L of 10% mannitol, a sugar alcohol, was introduced and garnered much expectation. However, colonic gas explosions during colonic surgery or therapeutic colonoscopy after mannitol preparation have been reported and the use of mannitol is now avoided. Bowel cleansing preparations with sorbitol have also been considered to be inappropriate in most advanced countries including the U.S. and Europe due to similar risks.

In the 1980s, bowel cleansing preparations comprising the ingestion of polyethylene glycol (PEG) formulated into a 4 L solution were developed. PEG formulations are still the most commonly used bowel cleansing agents worldwide.

The most serious problems with PEG preparations were their very large volume amounting to 4 L and difficulties of ingestion due to their disgusting taste. Such difficulty of ingestion gave rise to the wide-spread negative perception of bowel preparation, which has led people to fear or avoid colonoscopies.

Thus, various attempts have been made to reduce the volume of the PEG preparations to be ingested. For example, the required volume of the diluted PEG solution may be reduced to 3 L by including a stimulant laxative such as bisacodyl tablets in the regimen such that it is administered 6-12 hours prior to the ingestion of the PEG solution, or using a magnesium citrate (Trade name Citromag®) solution in combination, or adding ascorbic acid (Trade name MoviPrep®). In the case of MoviPrep® type bowel cleansing preparations, ascorbic acid and sodium ascorbate are added to make up for the anticipated reduction in cleansing efficacy. However, as the total amount of PEG contained in these bowel cleansing preparations is 200 g, the PEG content has decreased by only 15.3%, compared to the 236 g contained in the COLYTE powder which is to be administered in a 4 L volume. Thus, despite the decrease in the total volume of the diluted solution to be ingested, complaints of patient discomfort are more common than in the case of the COLYTE powder 4 L regimen because PEG is concentrated 1.7-fold.

In addition to such difficulties of ingestion, PEG preparations have not achieved satisfactory bowel cleansing power. Various studies show that the percentage of bowel cleansing with a PEG formulation achieving a cleansed level adequate for colonoscopy is approximately 70%. Such insufficient cleansing by PEG formulations has been demonstrated by a number of published studies. For instance, a study has reported that colonoscopy was hindered by the residual solid stool in the colon in 47.1% of patients who had their bowel cleansed with the PEG formulation "Colyte" <"Comparison between Conventional 4 L Polyethylene Glycol and Combination of 2 L Polyethylene Glycol and Sodium Phosphate Solution as a Colonoscopy Preparation", Seoul National University Bundang Hospital, Department of Internal Medicine, Seoul National University College of Medicine and Liver Research Institute, Jung Won Lee et al., *Korean J Gastroenterology*, 56, 299-306, 2010>.

In order to resolve such ingestion problems with the PEG preparations, picosulfate preparations comprising magnesium citrate were developed as bowel cleansing preparations. A big advantage with picosulfate preparations is that they have greatly improved taste and thus, unlike PEG preparations, their consumption causes little discomfort due to unpleasant taste. For that reason, picosulfate preparations are most commonly used in Europe, but their relatively poor bowel cleansing power is the biggest problem with these preparations. The recommended regimen for Ferring's Prepopik® (sodium picosulfate, magenisum oxide, and anhydrous citric acid) approved by the U.S. FDA indicates the total volume of ingestion amounting to 2.22 L, and according to actual use of this preparation it has been found to be problematic due to its relatively poor cleansing power compared to PEG solutions.

For such reasons, Picolight®, which has the same composition as Prepopik®, is often used in a total volume of 3.5 L in clinical settings, which is 1.5-fold higher than its recommended dose.

Moreover, picosulfate-containing bowel cleansing agents do not contain electrolytes and thus they rarely cause hyponatremia or hypopotassemia due to overdose, but severe side effects such as spasm, etc., have been reported. Due to the incorporation of magnesium into this preparation, hypermagenesemia may occur, and thus patients with renal disorders are banned from using the preparation.

Thus, picosulfate-containing bowel cleansing agents developed for solving the ingestion difficulties with PEG preparations have improved compliance but show poor bowel cleansing efficacy. Consequently, patients still have to ingest large amounts ranging from 2.3 L to 3.5 L, and there exist problems of electrolyte abnormalities and hypermagenesemia.

Attempts to overcome the above limitations of known bowel cleansing preparations have not been successful and, consequently, there is a strong need for the development of a novel bowel cleansing composition that has reliable cleansing powder, ease of administration, minimal side effects, and is safe.

DISCLOSURE OF THE INVENTION

In order to solve the problems in the prior art described above, the present invention has the objective of providing a novel bowel cleansing composition that is equipped not only with excellent cleansing efficacy to greatly improve the proportion of adequate bowel preparation that is still at about 70% at most but also with ease of administration owing to the improved taste as well as safety for the human body.

The present invention has another objective of providing a novel bowel cleansing composition which allows for economical mass production and commercialization.

The bowel cleansing composition according to the invention comprises as a first cleansing ingredient at least one sugar alcohol selected from xylitol, sorbitol, glycerol, erythritol, threitol, arabitol, ribitol, mannitol, galactitol, fucitol, iditol, inositol, volemitol, isomalt, maltitol, lactitol, maltotriitol, maltotetraitol, and polyglycitol; as a second cleansing ingredient ascorbic acid or a mixture of ascorbic acid and a salt of ascorbic acid; as a third cleansing ingredient picosulfate; and an aqueous solvent, wherein the concentration of the first cleansing ingredient is 10 g/L to 500 g/L based on the total composition, the concentration of the second cleansing ingredient is 15 g/L to 500 g/L based on the total composition, the concentration of the third cleansing ingredient is 1 mg/L to 100 mg/L, and the volume of the aqueous solvent is 0.1 L to 1.0 L.

By combining specific concentrations of a sugar alcohol, ascorbic acid, and picosulfate, the bowel cleansing composition according to the present invention displays superior cleansing efficacy as well as improved taste compared to existing bowel cleansing compositions. The bowel cleansing composition according to the present invention also greatly enhances the ease of administration and compliance by significantly reducing the volume of ingestion. In addition, the bowel cleansing composition according to the present invention improves patient discomfort by minimizing discomforts such as nausea, abdominal pain and vomiting during its consumption. By incorporating bicarbonates such as sodium bicarbonate, potassium bicarbonate, etc., electrolyte abnormalities such as hyponatremia, hypopotassemia, etc., which occurred with the existing bowel cleansing agents comprising picosulfate, can be prevented. Since the bowel cleansing composition of the present invention does not contain any magnesium, it can be safely used without severe side effects in patients with renal disorders.

In addition, by combining specific concentrations of a sugar alcohol and ascorbic acid, the present invention achieves superior cleansing efficacy and antibacterial effect relative to the volume of the consumed fluid, eliminating the risk of production of combustible gases in the colon after bowel cleansing preparation ensuring safety in the human body.

In particular, the most stressful part about the bowel cleansing preparation procedure from the viewpoint of the patients includes large volumes of ingestion, unpleasant taste, discomforts such as abdominal pain and vomiting. Picosulfate-containing bowel cleansing agents improve discomfort after administration but are still inconvenient in that large volumes amounting to 3.5 L need to be ingested due to their insufficient cleansing efficacy. By incorporating specific amounts of a sugar alcohol and ascorbic acid instead of magnesium citrate which had been additionally used in the existing picosulfate preparations, the present invention enhances bowel cleansing efficacy, thereby reducing the volume of ingestion to 2 L or less including water and thus leading to improved compliance. As such problems were solved, less patients complained of pain during administration. The present invention is significant in that, despite a greatly reduced volume being consumed, bowel cleansing efficacy was more improved and the potential risk of the generation of intestinal combustible gas can be eliminated as much as possible by using a specific sugar alcohol in combination with ascorbic acid.

As described above, the bowel cleansing composition of the present invention can make the bowel preparation procedure significantly easier and safer, thereby greatly contributing to the popularization of colonoscopy and, as a result, maximizing the early detection of colon cancer as well as the prevention of colon cancer by polypectomy. The bowel cleansing composition of the present invention may also be utilized in treating and alleviating constipation.

The preparation process of the invention allows for economical mass production and commercialization of the bowel cleansing composition.

DETAILED DESCRIPTION OF THE INVENTION

The present invention will now be described in detail with reference to the drawings.

The bowel cleansing composition according to the present invention comprises as a first cleansing ingredient at least one sugar alcohol selected from xylitol, sorbitol, glycerol, erythritol, threitol, arabitol, ribitol, mannitol, galactitol, fucitol, iditol, inositol, volemitol, isomalt, maltitol, lactitol, maltotriitol, maltotetraitol, and polyglycitol; as a second cleansing ingredient, ascorbic acid or a mixture of ascorbic acid and a salt of ascorbic acid; as a third cleansing ingredient picosulfate; and an aqueous solvent, wherein the concentration of the first cleansing ingredient is 10 g/L to 500 g/L based on the total composition, the concentration of the second cleansing ingredient is 15 g/L to 500 g/L based on the total composition; the concentration of the third cleansing ingredient is 1 mg/L to 100 mg/L, and the volume of said aqueous solvent is 0.1 L to 1.0 L.

Sugar alcohols used in the present invention as the first cleansing ingredient are a cleansing ingredient that works as a laxative when used at a high concentration. The sugar alcohol used as the first cleansing ingredient for the present invention is one or more selected from xylitol, sorbitol, glycerol, erythritol, threitol, arabitol, ribitol, mannitol, galactitol, fucitol, iditol, inositol, volemitol, isomalt, maltitol, lactitol, maltotriitol, maltotetraitol, and polyglycitol. In one aspect of the present invention, sugar alcohol used as the first cleansing ingredient may include xylitol or sorbitol or a mixture of xylitol and sorbitol.

With respect to the safety of sugar alcohols, along with mannitol, sorbitol has been deemed as a substance that should not be used for bowel preparation after an incidence of colonic gas explosion during a colopolypectomy procedure following bowel preparation using sorbitol was reported.

However, a review article by Ladas et al. shows that such incidence of explosion is not limited to mannitol or sorbitol, but occurs also after bowel preparation with a PEG formulation or a phosphate formulation. According to Ladas et al., a total of 20 gas explosions associated with bowel preparations were reported between 1952 and 2006, including four explosions during colopolypectomy of which two involved bowel preparation with PEG formulations, one with a phosphate formulation and another with mannitol <"Colonic gas explosion during therapeutic colonoscopy with electrocautery", Ladas S D, Karamanolis G, Ben-Soussan E., *World J Gastroenterol*, 13, 5295-8, 2007>.

Colonic gas explosions during surgery or therapeutic endoscopy after bowel preparation are believed to be caused by the combustible gases hydrogen and methane produced by the fermentation of sugar alcohols such as mannitol and sorbitol by intestinal bacteria. The explosive ranges for methane and hydrogen are 5-15 vol % and 4-75 vol %, respectively.

However, it has been demonstrated that hydrogen and methane gases are more likely to be produced when there are residues in the colon due to inadequate cleansing. It has been known that colonic gas explosions occurred not only with mannitol or sorbitol, but also after bowel preparation with formulations of PEG, which is another sugar alcohol, or phosphate, which is not a sugar alcohol. These facts indicate that the cause of colonic gas explosion cannot be limited to the use of particular colon cleansing preparations. Rather, the quality of colon cleansing has a significant effect in this regard. This is because when inadequate bowel cleansing leaves a lot of intestinal bacteria behind, substances such as sugar alcohols in the residual stool and the bowel cleansing solution are excessively degraded, producing hydrogen and methane in explosive concentrations.

Indeed, Nunes et al. reported that the cleansing efficacy of mannitol is inferior to PEG formulations, with the rate of adequate bowel cleansing being only 75% for mannitol as compared with 90% for PEG formulations when evaluated according to a scale proposed by the authors <"Comparative evaluation of bowel preparation for colonoscopy using mannitol and polyethylene glycol—a prospective study", Nunes B L, Belo S G, Pessoa M H, Lins Neto M A., *Rev Bras Coloproctol*, 28, 294-8, 2008>.

Given these observations, previously reported gas explosions after bowel preparation with mannitol or sorbitol are believed to have been affected by inadequate bowel cleansing.

However, by using a sugar alcohol as a first cleansing ingredient in combination with a second cleansing ingredient such as ascorbic acid, etc., and picosulfate as a third cleansing ingredient in specific concentrations, the present invention achieves superior cleansing efficacy and antibacterial effect relative to the volume of consumed fluid, eliminating the risk of explosion arising from inadequate bowel preparation ensuring safety.

The concentration of the first cleansing ingredient used in the present invention ranges from 10 g/L to 500 g/L, 20 g/L to 200 g/L, or 50 g/L to 150 g/L based on the total preparation, without limitation. If the concentration of the first cleansing ingredient is higher than the above range, production of the combustible gases hydrogen and methane may increase. If the concentration of the first cleansing ingredient is lower than the above range, it may lead to incomplete bowel cleansing.

Ascorbic acid, which is used as the second cleansing ingredient in the present invention, is a water-soluble vitamin known as vitamin C, an essential vitamin playing various roles in maintaining health. With an increasing interest in ascorbic acid, a variety of specialty beverages containing ascorbic acid are being marketed. These specialty beverages are manufactured to contain ascorbic acid at concentrations up to 10 mg/mL (i.e., 10 g/L).

In the present invention, however, ascorbic acid is the main cleansing ingredient which is used in a high concentration to work as a laxative and its antibacterial activity inhibits intestinal bacteria such that the production of colonic gases is minimized. For this purpose, the second cleansing ingredient is incorporated at a high concentration of 15 g/L to 500 g/L, 20 g/L to 300 g/L, or 30 g/L to 200 g/L based on the total composition. If the concentration of the second cleansing ingredient is higher than the above range, the excessively high acidity of the preparation may lead to excessive sour taste, making it difficult to consume the preparation, and may severely stimulate the stomach to cause nausea, retching, vomiting, and heartburn during the consumption of the preparation. On the other hand, if the concentration of the second cleansing ingredient is lower than the above range, the reduced antibacterial effect may lead to the excessive production of combustible gases in the colon.

A salt of ascorbic acid used as the second cleansing ingredient in the present invention refers to an alkaline metal or alkaline earth metal salt of ascorbic acid. Examples of the alkaline metal include, but are not limited to, sodium or potassium, and examples of the alkaline earth metal include, but are not limited to, calcium. The salt of ascorbic acid used in the present invention may be sodium ascorbate or calcium ascorbate.

A salt of ascorbic acid reduces the acidity of a solution compared to ascorbic acid alone, enhancing the bowel cleansing efficacy by inhibiting the absorption of ascorbic acid which is known to increase with acidity.

When the second cleansing ingredient is a mixture of ascorbic acid and a salt of ascorbic acid, the mass ratio of ascorbic acid to the salt of ascorbic acid may range from 99:1 to 60:40. If the mass ratio of ascorbic acid to the salt of ascorbic acid is outside the above range, excessive amounts of sodium, calcium, potassium or magnesium may be absorbed to the body, causing electrolyte abnormalities or resulting in hypercalcemia or hypermagnesemia.

Picosulfate used as the third cleansing ingredient in the present invention is used as a stimulant laxative. Picosulfate is usually administered once or twice daily at a dose of 7.5 mg at one time. The concentration of picosulfate used as the third cleansing ingredient in the present invention may be 1 mg/L to 100 mg/L, 10 mg/L to 80 mg/L, or 15 mg/L to 70 mg/L, based on the total composition.

The bowel cleansing composition of the present invention may additionally comprise an anti-foaming agent in order to remove colonic gases or bubbles frequently seen after bowel preparation. In one aspect of the present invention, examples of suitable anti-foaming agent includes, without limitation, simethicone.

In general, if a substantial amount of bubbles appear during screening colonoscopy, a diluted simethicone solution is prepared and injected into the colon through a small channel in the scope. Another approach involves separate administration of a separately provided simethicone preparation at the last stage of bowel preparation. However, when diluted simethicone is injected through a channel in the scope during the procedure, the area that can be covered by a single application of diluted simethicone is very limited. Thus, if the bubbles are formed across a large area, inconvenience arises as the application of diluted solution may need to be repeated as many as ten times or more. Even when the simethicone preparation is separately administered at the last stage of bowel preparation, the volume of the preparation is typically as small as 10 ml, which may be insufficient to prevent the formation of bubbles throughout the colon.

To address this problem, the present invention incorporates a diluted anti-foaming agent such as simethicone into the bowel cleansing composition so that foaming is very effectively inhibited across the regions of colon reached by the bowel cleansing liquid even with a small volume of the anti-foaming agent.

The concentration of the anti-foaming agent used in the present invention may be 100 mg/L to 2 g/L, 150 mg/L to 1.5 g/L, or 200 mg/L to 1 g/L based on the total preparation in the case of simethicone, but is not limited to the above ranges in the case of anti-foaming agents other than simethicone. If the concentration of the anti-foaming agent exceeds the upper limit of the above range, it may cause adverse effects such as abdominal pain, rash, swelling of the face or tongue, breathing difficulties, etc.

Aqueous solvents that can be used in the present invention include water, carbonated water, alkaline ionized water, and beverages, for example. There is no particular limitation on the kind of beverage as long as the effect of the present invention can be achieved. Examples of beverages include coffee, various juices, cola, clear sodas, and gin and tonic. In one aspect of the present invention, carbonated water or alkaline ionized water can be used as the aqueous solvent. Working independently as a laxative, carbonated water is known to be effective in improving constipation in elderly people suffering from chronic constipation. Alkaline ionized water may increase the cleansing efficacy by partially neutralizing the acidity of the bowel cleansing composition of the present invention, leading to reduced absorption of ascorbic acid.

The volume of the aqueous solvent can be, without limitation, 0.1 L to 1.0 L, 0.1 L to 0.9 L, 0.2 L to 0.8 L, or 0.3 L to 0.7 L. If the volume of the solvent is less than 0.1 L, ingredients may not be completely dissolved in the solvent. If the volume of the solvent is greater than 1.0 L, the large volume may lead to reduced compliance.

The bowel cleansing composition of the present invention may additionally comprise ingredients for improving compliance and alleviating upper gastrointestinal symptoms such as nausea, retching and vomiting that are frequently observed during bowel preparation.

Because the bowel cleansing composition of the present invention containing a large amount of ascorbic acid and citric acid is high in acidity and may be difficult to consume due to excessive sour taste, it may comprise a bicarbonate salt such as sodium bicarbonate and potassium bicarbonate to neutralize the acidity.

Sodium bicarbonate can be used at a concentration ranging from 0.1 g/L to 10 g/L based on the total preparation. If used beyond the above range, it may lead to reduced compliance due to excessive saltiness and cause hypernatremia. Potassium bicarbonate can be used at a concentration ranging from 0.1 g/L to 20 g/L based on the total preparation. If used beyond the above range, it can cause hyperkalemia due to the intake of potassium exceeding its daily recommended dose. Hyperkalemia poses the risk of heart disorders, for example.

The bowel cleansing composition of the present invention may further comprise an extract, powder or concentrate of ginger, peppermint, chamomile or the like in the form of aqueous solution for the purpose of enhancing the compliance by alleviating symptoms such as nausea, vomiting and abdominal pain. These ingredients work as gastrointestinal soother and can be incorporated at a concentration of 5 g/L to 50 g/L based on the total bowel cleansing composition. If used excessively beyond the above range, such gastrointestinal soothers may reduce the cleansing efficacy by inhibiting bowel movement.

The bowel cleansing composition of the present invention may further comprise known cleansing ingredients or adjuncts for augmenting the cleansing effect. Examples of additional cleansing ingredients and adjuncts include citric acid, magnesium component such as magnesium oxide, docusate sodium, senna extract (e.g., sennoside), aloe extract (e.g., aloin), garlic extract (e.g., alliin and allicin) etc. and pectin, zinc component such as zinc oxide, caffeine, etc.

Citric acid is a natural substance present in citrus fruits in high concentrations. It makes sour taste and is used as a preservative in a variety of beverages and food. Citric acid is classified as a very safe substance, and the FDA and the FAO/WHO have recognized that the ingestion of excessive amounts of citric acid causes little harm. In the bowel cleansing composition of the present invention, citric acid can be incorporated as an additional cleansing ingredient working as a laxative. In this case, the concentration of citric acid may be 1 g/L to 15 g/L based on the total preparation. If its concentration exceeds the above range, patient compliance may be reduced due to heartburn and strong sour taste.

Magnesium is also a substance than can function as a laxative. However, it should be used with caution in people with renal disorders because administering an excess amount greater than 3 g at one time may cause adverse effects from hypermagnesemia.

Pectin and zinc can enhance the laxative effect of ascorbic acid by inhibiting its gastrointestinal absorption. Pectin can be used at a concentration of 0.1 g/L to 2 g/L based on the total preparation, and may not be dissolved if used at a concentration greater than the above range. Zinc oxide can be used at a concentration of 10 mg/L to 400 mg/L based on the total preparation, and its excessive intake beyond the above range may cause vomiting, retching, etc.

Caffeine may be used to fight the sluggishness that may be felt during bowel preparation and enhance the cleansing efficacy. Up to 30 mg of caffeine can be used based on the total preparation. Excessive intake of caffeine beyond the above range can cause tachycardia, anxiety, sleep disturbance, etc.

Substances that may be used as adjunctive laxatives also include docusate sodium (10 mg/L to 400 mg/L. Excessive intake can cause vomiting, abdominal pain, etc.), senna extract (sennoside, 10 mg/L to 50 mg/L, Excessive intake can cause vomiting, abdominal pain, etc.), aloe extract (aloin, 10 mg/L to 50 mg/L. Prolonged excessive intake can cause reduced bowel function), garlic extracts (alliin and allicin, 10 mg/L to 5 g/L, Excessive intake can cause severe abdominal pain and vomiting), and the like.

The bowel cleansing composition of the present invention may include sweeteners to improve taste. Examples of suitable sweeteners include, without limitation, sucralose, maltodextrin, glucose, sucrose, dextrose, saccharin, aspartame, and stevia. Such sweeteners can be used in a range from 0.01 mg/L to 10 g/L based on the total bowel cleansing composition. Using an excessive amount beyond the above range may cause discomforts such as nausea and retching.

The bowel cleansing composition of the present invention may additionally include suitable amounts of edible fruit flavorings to enhance compliance. Such fruit flavorings may be strawberry flavor, orange flavor, apple flavor, grape flavor, lemon flavor, banana flavor, cherry flavor, etc.

The bowel cleansing composition of the present invention may additionally comprise a suitable amount of antioxidant to prevent the oxidation of ascorbic acid. Such antioxidant includes, without limitation, ferulic acid, amino acids such as glycine and histidine, hyaluronic acid, and tocopherol.

In addition, the bowel cleansing composition of the present invention may additionally comprise a chelating agent to chelate the trace amounts of iron and copper ions potentially contained in the aqueous solvent. Examples of such chelating agents include, without limitation, the Versene CA chelating agent (The Dow Chemical Company).

The bowel cleansing composition according to the present invention can be a one-part product or a two-part product.

In one aspect of the present invention, the bowel cleansing composition can be packaged as a one-part product in which the entire ingredients including a first cleansing ingredient, a second cleansing ingredient, and a third cleansing ingredient, and, as necessary, an anti-foaming agent, a gastrointestinal soother, and other additives are packaged in a container together with an aqueous solvent.

In another aspect of the present invention, the bowel cleansing composition can be packaged as a two-part product. For example, the first cleansing ingredient, the second cleansing ingredient, and the third cleansing ingredient may be packaged together while the aqueous solvent is separately packaged; the second cleansing ingredient and the aqueous solvent are packaged together while the first cleansing ingredient and the third cleansing ingredient are separately packaged; the first and third cleansing ingredients and the aqueous solvent are packaged together while the second cleansing ingredient is separately packaged; the first and third cleansing ingredients and part of the aqueous solvent are packaged together while the second cleansing ingredient and part of the aqueous solvent are packaged together; or the first, second, and third cleansing ingredients and part of the aqueous solvent may be packaged together while the remaining part of the aqueous solvent is separately packaged, but not limited thereto. In addition, anti-foaming agent, gastrointestinal soother, and other additives can be incorporated into the two-part product, as necessary, in various combinations.

A method of formulating the bowel cleansing composition as a two-part product that is packaged in the form of highly concentrated solution and a vehicle and using the product is now explained. For example, the entire ingredients including the first cleansing ingredient, second cleansing ingredient and third cleansing ingredient, and, if necessary, the anti-foaming agent, gastrointestinal soother, and other additives are dissolved in a minimal amount of an aqueous solvent to give a highly concentrated solution, and users may dilute the solution in a beverage (making up the remaining volume as an aqueous solvent) they have chosen as vehicle. In such a case, the volume of the aqueous solvent for forming the highly concentrated solution may be 0.05 L to 0.2 L, and the amount of the beverage of the user's choice, i.e., vehicle may be the remaining volume for an aqueous solvent. If necessary, each solid ingredient of the composition is separately packaged as well as the aqueous solvent, and users can mix the entire ingredients at the time of ingestion. Various other forms of packaging can also be used and the form of the two-part product is not limited by the packaging methods described above.

In manufacturing the bowel cleansing composition according to the present invention, the entire ingredients including the first cleansing ingredient, the second cleansing ingredient, and the third cleansing ingredient, and as necessary, the anti-foaming agent, gastrointestinal soother, and other additives can be mixed with the aqueous solvent at the same time, or each ingredient can be separately prepared and then mixed stepwise.

For example, a process for preparing the bowel cleansing composition according to the present invention may comprise the steps of forming a first mixture comprising a sugar alcohol as a first cleansing ingredient; forming a second mixture comprising ascorbic acid or ascorbic acid and a salt of ascorbic acid as a second cleansing ingredient; forming a third mixture comprising picosulfate as a third cleansing ingredient; as necessary, forming a fourth mixture comprising an anti-foaming agent; as necessary, forming a fifth mixture comprising a gastrointestinal soother; and mixing the first mixture to fifth mixture with an aqueous solvent to form a bowel cleansing composition.

In another aspect of the present invention, a process for preparing the bowel cleansing composition of the present invention may additionally include the steps of mixing in advance the first mixture to fifth mixture in any combinations prior to mixing the first, second, and third mixtures, and as necessary the fourth and fifth mixtures, with an aqueous solvent.

In a further aspect of the present invention, a process for preparing the bowel cleansing composition of the present invention may involve, for example, preparing in advance a highly concentrated solution comprising the first, second, and third mixture, and as necessary, the fourth and fifth mixtures, and part of the aqueous solvent, and then adjusting the solution to the above-described specific concentrations and quantities by diluting with various beverages at the time of ingestion. In this case, the type of beverage that users can choose as a vehicle is not particularly limited as long as it is an aqueous solvent, including water, carbonated water, alkaline ionized water and a beverage, etc., and the beverage may be the same as or different from the aqueous solvent in the highly concentrated solution. There is no particular limitation on the kind of beverage as long as the effect of the present invention can be achieved. Examples of beverages include drip coffee, various juices, cola, clear sodas, and gin and tonic.

In the process for preparing the bowel cleansing composition of the present invention, the method of mixing for the individual ingredients, particle shape and size of solids, pH, preparation temperature, agitation conditions, containers, packaging material, vacuum packaging or gas-substituted packaging, and other packaging specifics may be adjusted as necessary depending on the form, type, shipping and storage method of the bowel cleansing composition to be prepared.

A dosing regimen for the bowel cleansing composition of the present invention may involve, without limitation, consuming 50-100 cc of the composition every 5-10 minutes for a total of 5-10 doses, starting at 3-5 hours before the scheduled colonoscopy depending on the bowel sensitivity of the subject. While not intended to be limiting, the bowel cleansing composition of the present invention may be ingested over a time period of, for example, 1 hour to 1.5 hour and a suitable amount of bottled water or the like may be additionally taken in case of thirst.

By comprising specific concentrations of a sugar alcohol, ascorbic acid, and picosulfate, the bowel cleansing composition of the present invention displays enhanced bowel cleansing efficacy despite a greatly reduced volume of ingestion. The bowel cleansing composition of the present invention also achieves convenience of administration by requiring a very small volume of ingestion. In addition, the bowel cleansing composition of the present invention causes no or minimal discomfort such as nausea, retching, and bloating as it does not contain unpalatable ingredients, and is safe as it inhibits the production of combustible gases in the colon.

The preparation process of the present invention allows for the economical mass production and commercialization of a high performance bowel cleansing composition.

As the bowel cleansing composition of the present invention has excellent cleansing efficacy, ease of administration and safety, it can be utilized for bowel preparation prior to colonoscopy or the like, for preparation prior to colonic surgery and anal surgery for hemorrhoid or the like as well as for the treatment and alleviation of diseases such as chronic and acute constipation.

The present invention will now be described in more detail with reference to examples. It is to be understood, however, that the examples are provided to illustrate embodiments of the present invention and not intended to limit the scope of the invention.

Example 1

In 100 mL of distilled water as solvent, 45 g of xylitol, 25 g of ascorbic acid, 20 mg of picosulfate, 200 mg of simethicone, 1.4 g of sodium bicarbonate, 3.4 g of potassium bicarbonate, and 20 mg of sucralose were mixed to form 150 mg of a highly concentrated solution, and 350 ml of carbonated water was used as a separate vehicle to prepare a two-part bowel cleansing composition.

Mixing was conducted by mixing all the ingredients in powder form at the same time and then pouring solvent to dissolve them. Caution is needed because a large amount of carbon dioxide ($CO_2$) gas generated by the neutralization reaction between the acidic ascorbic acid and basic bicarbonate salt causes extensive foaming. Preparing a 1:10 diluted solution of Gasocol® containing the anti-foaming agent simethicone beforehand and adding it suitably while mixing can successfully prevent foaming, thereby facilitating the mixing process. Since a pharmaceutical simethicone product containing about 30% of silicon is insoluble in water, Gasocol®, which is a liquid formulation comprising simethicone as the main component, was used instead in this example.

Comparative Reference Example 1

For in vitro tests to assess the safety of sugar alcohols used as a first cleansing ingredient in the present invention, Comparative Reference Example 1 was prepared for comparison with the solution of Example 1.

Comparative Reference Example 1 refers to a 10 mL PICOLYTE solution which is prepared by diluting the active ingredient in bottled water according to the recommended regimen. The concentration of the active ingredient is the same as its concentration used in bowel cleansing.

Experimental Example 1: Safety Tests Concerning the Production of Combustible Gases (In Vitro)

Measurement of Concentrations of Hydrogen and Methane Gases

With regard to safety tests regarding the production of intestinal combustible gases, it is not easy to obtain suitable specimens from the subject or assess colonic gas during colonoscopy and it is not reasonable to conclude that the observed differences are attributable to the difference in the bowel cleansing solution based only on results obtained from a limited number of cases while the conditions of individual subjects after bowel preparation are widely different. Thus, the potential risk of the composition prepared in the Example was indirectly investigated by in vitro tests which can be conducted under identical conditions.

For this purpose, aliquots of the solutions from Example 1, Comparative Reference Example 1, and Control (bottled water) were mixed with a diluted solution of stool collected from 5 people, and 20 mL of the diluted solution each was stored in 500 mL containers for 18 hours at room temperature. Then, gas concentrations in each container were measured using a gas detector. The diluted solutions of stool were prepared by sampling stools from fiver different subjects and diluting 3 g of the stool from each subject in 100 mL of bottled water, giving a total of 5 different diluted solutions of stool.

Detailed test protocols are described below.

For each of the five subjects whose stool samples were taken, a 10 mL aliquot of the diluted solution of stool was placed in three containers, providing three containers holding the same diluted solution of stool. As a result, a total of 15 containers holding the diluted solutions of stool from the five subjects were prepared.

For each subject, 10 ml each of the test solutions from Example 1, Comparative Reference Example 1 (PICOLYTE), and Control (bottled water) were added to the three containers holding the same diluted solution of stool, respectively.

After mixing the diluted solutions of stool with the respective test solutions, the containers were sealed by tight capping and stored for 18 hours at room temperature.

Then, the concentrations of hydrogen and methane in each container were measured using the Geotech GA5000 gas analyzer (Landtech, UK). Geotech GA5000 gas analyzer can measure methane in vol % unit and hydrogen in the range of 0-1000 ppm.

Measurement of the gas concentrations in the 15 containers in total gave average measurements for the concentrations of the combustible gases, hydrogen and methane, as shown in Table 1.

TABLE 1

|  | Example 1 | Comparative Reference Example 1 (PICOLYTE) | Control (Bottled water) |
| --- | --- | --- | --- |
| Hydrogen (ppm) | 0 | 451.3 | 173.6 |
| Methane (Vol %) | 0.13 | 0.16 | 0.14 |

As can be seen from Table 1, the bowel cleansing composition of Example 1 gave no detectable hydrogen, as well as a methane concentration of 0.13%, which is lower than that of the control and that of the picosulfate bowel cleansing solution of Comparative Reference Example 1. That is, these results show that the bowel cleansing composition of the present invention is the safest with respect to the generation of colonic combustible gases.

Bacterial Culture Test

Following the measurement of gas concentration as described above, the mixed solutions in the containers were submitted to two testing institutions, i.e., a laboratory at the Seoul Medical Science Institute (SCL), a CAP accredited and Korean Society for Laboratory Medicine (KSLM)/Laboratory Medicine Foundation accredited institution, and the KSLM accredited Green Cross Laboratories, where they were cultured for 48 hours and measured for the resulting colony counts.

Figure 1:
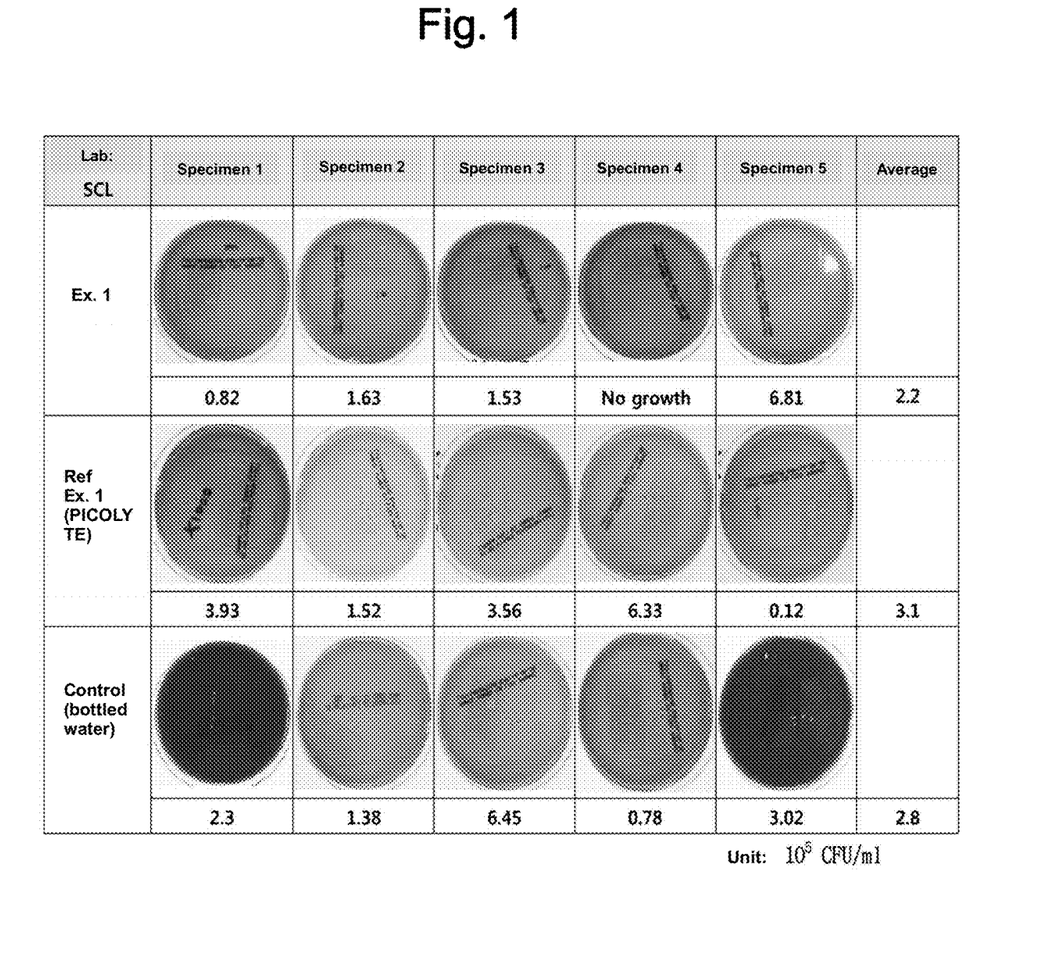
FIG. 1 and FIG. 2 are photographs obtained from the respective laboratories which show the results of culturing intestinal bacterial after treatment with the bowel cleansing compositions according to one Example and the Comparative Examples.
Figure 2:
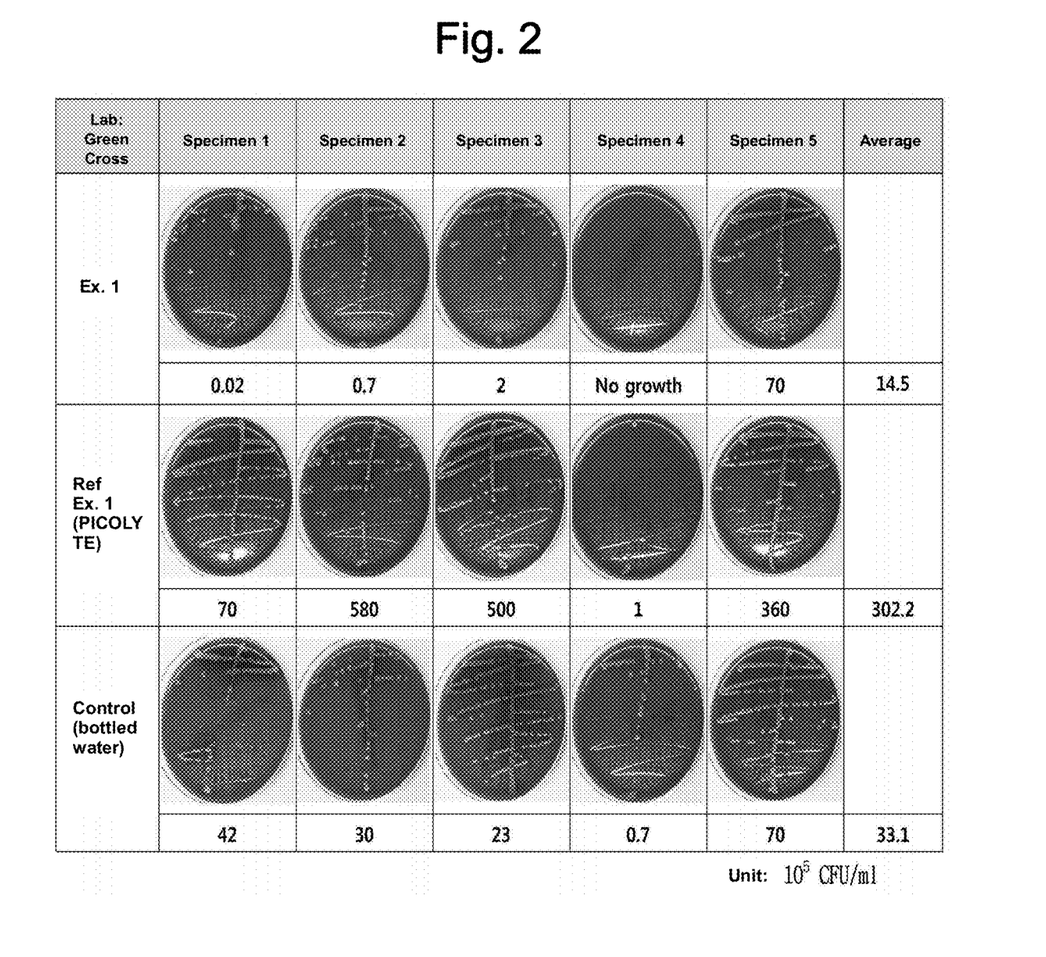

Averages of the colony counts for the respective test solutions are listed in Table 2. In addition, FIG. 1 and FIG. 2 show the results from the culture of intestinal bacterial for Example 1, Comparative Reference Example 1, and Control, in accordance with the respective laboratories.

TABLE 2

|  |  | Example 1 | Comparative Reference Example 1 (PICOLYTE) | Control (bottled water) |
| --- | --- | --- | --- | --- |
| Colony counts (CFU/mL) | SCL | 2.2 | 3.1 | 2.8 |
|  | Green Cross Laboratories | 14.5 | 302.2 | 33.1 |

(Unit: $10^5$ CFU/ml)

The above colony count results clearly demonstrate the antibacterial effect of the bowel cleansing composition according to the present invention. Specifically, in case of Example 1, the colony counts of the cultures of the diluted solutions of stool in the five subjects were all lower than those of Comparative Reference Example 1 using PICOLYTE and even those of the Control group. That is, it can be seen from Example 1 that bacteria capable of producing combustible gases such as hydrogen or methane were significantly suppressed. Although obtained from in vitro tests, these results demonstrate that with respect to the production of combustible gases in the colon, the bowel cleansing composition of the present invention is safer than any of the existing bowel cleansing agents.

With respect to Comparative Reference Example 1 in which PICOLYTE was used, it was found that the counts of the cultured colonies were higher than those of the Control group in natural state. This has not yet become an issue but suggests the potential risk of this type of bowel cleansing agent to promote the generation of combustible gas. These results show that the bowel cleansing agent of the present invention is very safe with respect to the generation of combustible gas although it contains a sugar alcohol.

The above results demonstrate that the composition of Example 1 comprising xylitol, ascorbic acid, and picosulfate as main ingredients is very safe with regard to intestinal bacterial growth and the resulting production of combustible gases in the colon.

Such excellent antibacterial effect suggest that the bowel cleansing composition of the present invention may greatly contribute to reducing the incidence of postoperative infections when it is used as a laxative for bowel preparation before colonic surgery. Because contamination from the bowel contents may occur during colonic surgery, the preoperative administration of antibiotics to prevent surgical site infection due to such contamination is established as the standard. However, if the bowel cleansing composition of the present invention is used for preoperative bowel preparation, it inhibits bacteria in the bowel contents, reducing the possibility of infection even when contamination from the bowel contents occurs.

Considering the fact that the existing bowel cleansing liquids are used not only for bowel cleansing prior to colonoscopy but also as the main laxative for preoperative bowel preparation before colonic surgery, the above-described effect may enhance the significance of the bowel cleansing composition of the present invention.

From the two in vitro safety tests described above, it can be seen that the novel bowel cleansing composition according to the present invention has the lowest risk as it minimizes the production of combustible hydrogen and methane gases compared to conventional colon cleansing preparations and inhibits bacterial growth.

Comparative Examples 1 and 2

Comparative Examples 1 and 2 were prepared for comparative experiments concerning the ease of administration, bowel cleansing efficacy and safety of the bowel cleansing composition of the present invention.

Specifically, for in vivo experiments, commercially available bowel cleansing products PICOLYTE and CoolPrep were respectively mixed with water in their recommended mixing amounts to prepare the bowel cleansing compositions for Comparative Examples 1 and 2. The identities of the bowel cleansing agents and the volume of water used in Comparative Examples 1 and 2 are listed in Table 3.

TABLE 3

|  | Bowel cleansing agent | Volume of water |
| --- | --- | --- |
| Comparative Example 1 | PICOLYTE 2 pouches | 2.3 L |
| Comparative Example 2 | CoolPrep 4 pouches | 3 L (including 1 L water for additional ingestion) |

PICOLYTE: Pharmbio Korea Co., Ltd., 16.37 g per pouch
CoolPrep: Taejoon Pharm Co., Ltd., 56.402 g per pouch The bowel cleansing compositions prepared in Example 1 and Comparative Examples 1 and 2 were evaluated for their cleansing performance and compliance.

Specifically, the bowel cleansing efficacy, ease of administration, and safety of Comparative Example 1 (n=63), Comparative Example 2 (n=49), and Example 1 (n=161) were evaluated in patients undergoing colonoscopy. Detailed dosing regimens for Example 1 and Comparative Examples 1 and 2 are described below.

In the dosing regimen of Example 1, starting from 5 hours before the scheduled examination, a total of 500 ml of the bowel cleansing solution was ingested at a rate of 100 ml (5 mouthfuls, one half of a paper cup) every 30 minutes for a total of 5 times as a general rule. After ingestion of 100 ml of the bowel cleansing solution, 200 ml of bottled water was additionally ingested every 15 minutes. According to this regimen, ingestion of the bowel cleansing agent took 120 minutes in total.

With respect to Comparative Example 1, i.e., PICOLYTE 2.3 L, one pouch provided in the product was ingested after dilution in 150 ml of water at 7 PM the day before the examination followed by additional 1 L of water over one hour, and the process was repeated once on the day of examination at 5 hours before starting the examination.

With respect to Comparative Example 2, i.e., CoolPrep 3 L, 1 L of the prepared solution was ingested over 1 hour (250 ml of solution every 15 minutes) at 7 PM the day before the examination, and another 1 L of the prepared solution was ingested over 1 hour on the day of examination at 5 hours before starting the examination. The patients were instructed to drink 500 ml of water in the evening and morning of the day of examination after completing the ingestion of the diluted solution.

Experimental Example 2: Bowel Cleansing Efficacy

Bowel cleansing efficacy was assessed in two aspects: ① colon cleanliness and ⓪ the amount of bubbles.

Colon Cleanliness

Figure 3:
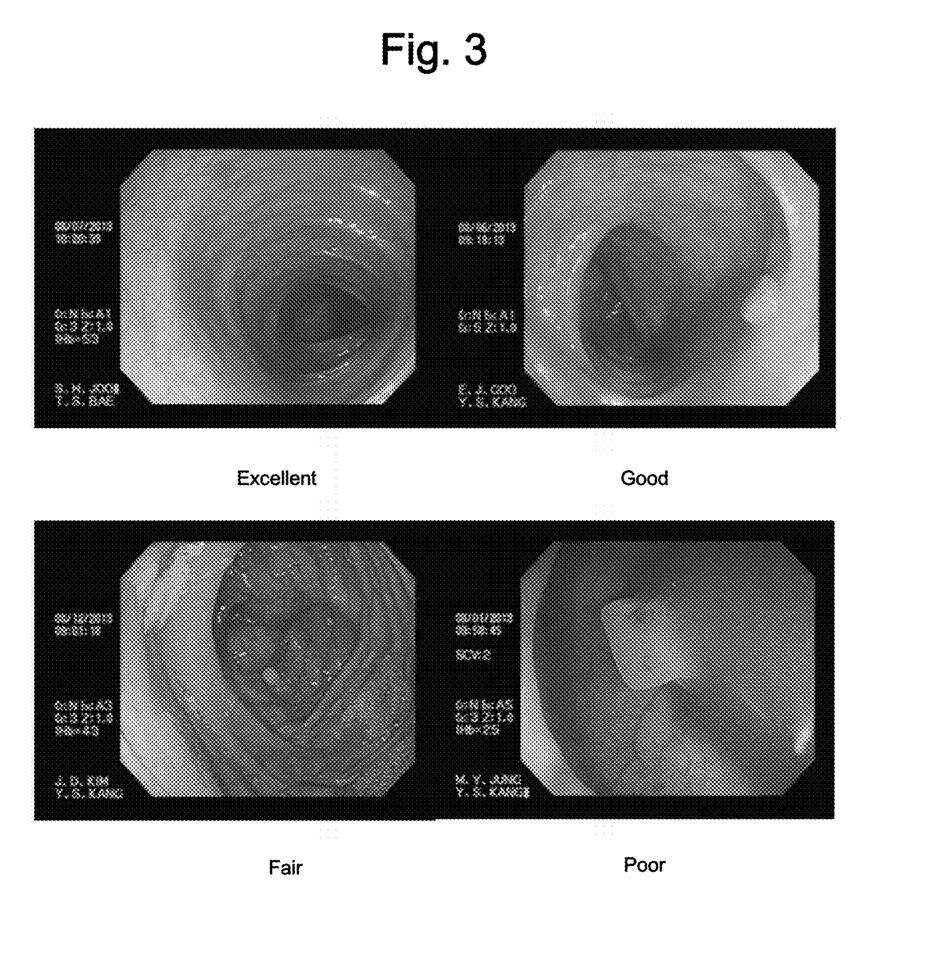
FIG. 3 shows photographs representing the cleanliness of the colon following the ingestion of the bowel cleansing compositions according to one Example and the Comparative Examples.

For the assessment of colon cleanliness, a surgeon evaluated the level of colon cleanliness of a patient using a five-point scale (Excellent, Good, Fair, Poor, Fail) according to the criteria shown in Table 4 and FIG. 3. For a fair evaluation, the evaluation was carried out in a blind test in which the surgeon performing the colonoscopy was not informed of the identity of the bowel cleansing composition consumed by the individual patients.

TABLE 4

| | |
| --- | --- |
| Excellent | Very thorough cleansing allowing the detection of even small lesions |
| Good | Slightly less clean than "Excellent" while sufficiently clean to allow the detection of even small lesions |
| Fair | Possible to miss one or two lesions ≤5 mm |
| Poor | Possible to miss lesions ≥5 mm due to poor cleanliness but no possibility of missing malignant lesions, i.e., colon cancer |
| Fail | Requiring repeat preparation because of the possibility of missing malignant lesions, i.e., colon cancer |

The results of the colon cleanliness assessment according to the criteria show in Table 4 and FIG. 3 are provided in Table 5.

TABLE 5

| | Colon cleanliness (%) | | | | |
| --- | --- | --- | --- | --- | --- |
| Sample | Excellent | Good | Fair | Poor | Fail |
| Example 1 | 36.7 | 55.7 | 5.7 | 1.9 | 0 |
| Comparative Example 1 (PICOLYTE) | 15.9 | 41.3 | 22.1 | 15.9 | 4.8 |
| Comparative Example 2 (CoolPrep) | 16.3 | 51 | 22.5 | 10.2 | 0 |

Figure 4A:
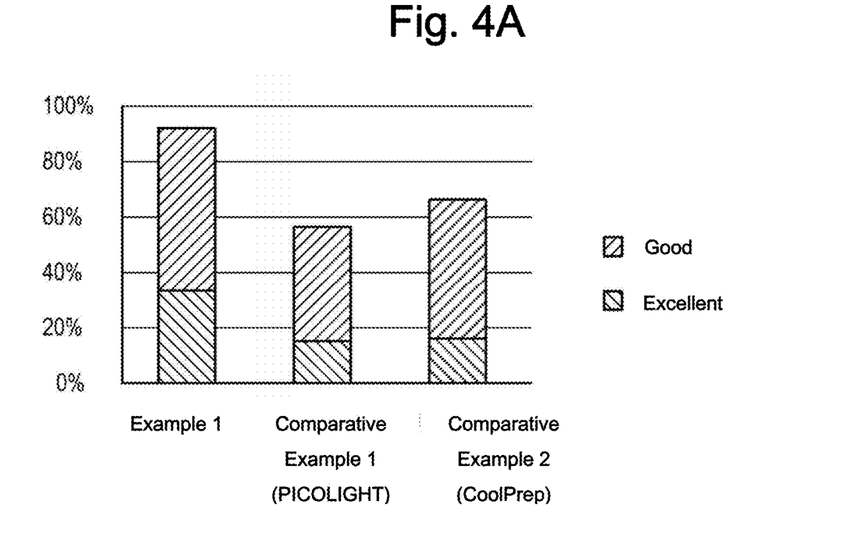
FIG. 4A and FIG. 4B show graphs representing the rates of effective and insufficient bowel cleansing following the consumption of the bowel cleansing compositions according to one Example and the Comparative Examples.
Figure 4B:
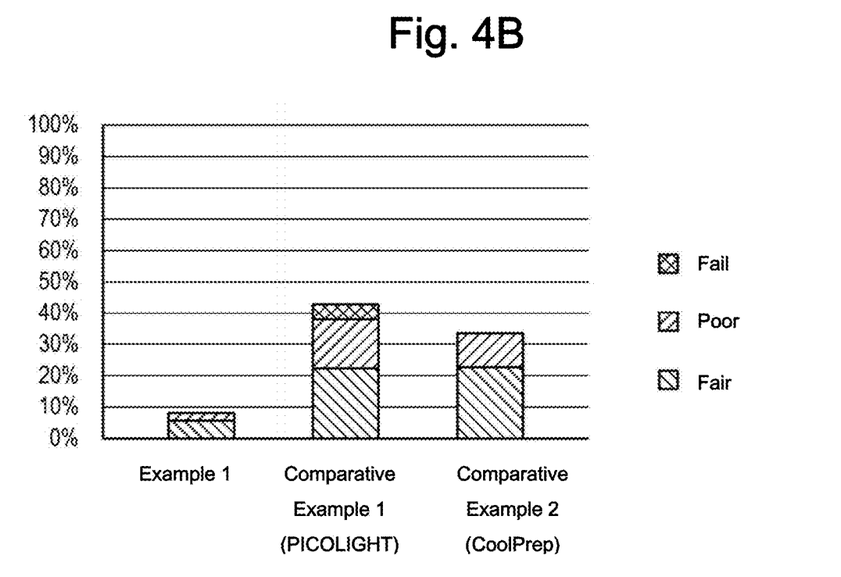

FIG. 4A and FIG. 4B present the above results classified as "effective bowel cleansing" referring to conditions adequate for colonoscopy and "insufficient bowel preparation" referring to conditions unsatisfactory or impossible for accurate colonoscopy. "Effective bowel preparation" includes conditions rated as Excellent or Good, and "insufficient bowel preparation" includes conditions rated as Fair, Poor, or Fail.

As can be seen from Table 5, FIG. 4A and FIG. 4B, the rate of effective bowel preparation was the highest in Example 1 as 92.4%, while Comparative Example 2 was found to be the worst in cleanliness with a rate of effective bowel cleansing of 57.2%. Comparative Example 2 showed a rate of effective bowel cleansing of 67.3%. These results fairly correspond with reports in some foreign research articles indicating that the PEG preparations and phosphate preparations show rates of adequate bowel cleansing of about 70~75% <"Colonoscopy preparation", ASGE technology committee, *GASTROINTESTINAL ENDOSCOPY*, 69 (No. 7):1201-1209, 2009>.

However, insufficient bowel preparation as is seen with Comparative Examples 1 and 2 actually causes serious problems because it does not allow for accurate colonoscopy. Normally, colonoscopy is repeated every 4-5 years. If the results of colonoscopy performed after a painful bowel preparation are inaccurate such that polyps or early colon cancer are not detected, the diseases are usually neglected for 4-5 years until the next screening examination, potentially allowing for polyps to advance to cancer or for the early colon cancer to advanced colon cancer.

Amount of Bubbles

Figure 5:
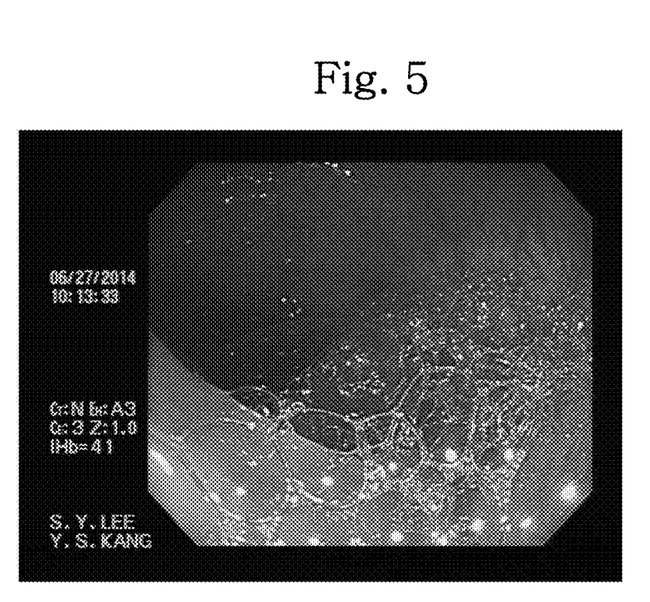
FIG. 5 is a photograph showing a substantial amount of intracolonic bubbles generated after consumption of a bowel cleansing composition prepared according to prior art.

In addition to colon cleanliness, another major factor for accurate colonoscopy is the presence of bubbles in the colon. Almost all bowel cleansing agents tend to generate bubbles in the colon following bowel preparation. Accordingly, the prevention or removal of such bubbles is required in order to thoroughly inspect the colonic lumen to detect even small lesions. The presence or absence as well as the extent of bubbles were observed after ingestion of the bowel cleansing composition of Example 1 and Comparative Examples 1 and 2, and the results are shown in Table 6. The extent of bubbles were rated on a three-point scale of "None," "Some," and "Substantial." FIG. 5 is a photograph showing a substantial amount of intracolonic bubbles generated after the consumption of the bowel cleansing composition of Comparative Example 1.

TABLE 6

| | Amount of bubbles (%) | | |
|---|---|---|---|
| Sample | None | Some | Substantial |
| Example 1 | 92.8 | 7.2 | 0 |
| Comparative Example 1 (PICOLYTE) | 35.7 | 33.9 | 30.4 |
| Comparative Example 2 (CoolPrep) | 32.5 | 27.5 | 40 |

As shown in the above results, in case of Example 1, bubbles were not generated in 92.8% of the subjects, but in case of Comparative Examples 1 and 2, the percentage of subjects developing no bubbles was as low as about ⅓. In particular, substantial amounts of bubbles were formed to the extent that examination was greatly interfered in more than one in three subjects. When bubbles form, they can be washed away using pharmaceutical agents during colonoscopy. However, it takes a substantial amount of effort and time as the area that can be washed at one time is limited. Thus, excessive bubble formation interferes with the smooth progress of colonoscopy and also becomes the reason for missing small lesions. As for the bowel cleansing composition of Example 1, the almost complete prevention of bubble formation allows for more time to be allotted to the observation of lesions while at the same time reducing procedure time, and also enhances the disease detection rate because the clear vision facilitates the detection of small lesions.

Experimental Example 3: Ease of Administration

Ease of administration was assessed in four aspects: ① taste of the cleansing agent, ② discomfort after administration, ③ willingness to recommend to family, and ④ need for improvement.

Taste of Cleansing Agents

In a questionnaire, the subjects were asked to subjectively rate the taste of the bowel cleansing agents on a three-point scale of "Very unpleasant," "slightly unpleasant," and "Fair." The percentages of each response category are shown in Table 7.

TABLE 7

| | Taste of bowel cleansing compositions (%) | | |
|---|---|---|---|
| Sample | Very unpleasant | Slightly unpleasant | Fair |
| Example 1 | 0 | 4.9 | 95.1 |
| Comparative Example 1 (PICOLYTE) | 0 | 6.1 | 93.9 |

TABLE 7-continued

| | Taste of bowel cleansing compositions (%) | | |
|---|---|---|---|
| Sample | Very unpleasant | Slightly unpleasant | Fair |
| Comparative Example 2 (CoolPrep) | 14.3 | 53.1 | 32.6 |

As shown in the above results, 95.1% of the subjects rated the taste of the bowel cleansing agent as "Fair" for Example 1, while 93.9% of the subjects rated the taste of the bowel cleansing agent as "Fair" for Comparative Example 1. For Comparative Example 2, however, only 32.6% of the subjects rated the taste of the bowel cleansing agent as "Fair".

Discomfort after Administration

Discomforts after administration were classified into 4 groups of abdominal pain, bloating, vomiting, and thirst. In a questionnaire, the subjects were asked to indicate self-perceived discomforts, and the percentages of each response category are shown in Table 8.

TABLE 8

| | Discomfort after administration (%) | | | |
|---|---|---|---|---|
| Sample | Abdominal pain | Bloating | Vomiting | Thirst |
| Example 1 | 8 | 28 | 2 | 25 |
| Comparative Example 1 (PICOLYTE) | 17 | 38 | 2 | 27 |
| Comparative Example 2 (CoolPrep) | 10.4 | 10.4 | 37.5 | 18.8 |

As can be seen from Table 8, Example 1 caused a level of discomfort that is lower than or similar to existing bowel cleansing agents with regard to all categories such as abdominal pain, bloating, vomiting, and thirst. Vomiting was quite frequent in Comparative Example 2, which appears to be associated with the unpleasant taste of PEG preparations.

Willingness to Recommend

In a questionnaire, subjects were asked if they are willing to recommend the bowel cleansing composition they used to their family, and the percentages of subjects who answered negatively are shown in Table 9.

TABLE 9

| Sample | Non-recommendation (%) |
|---|---|
| Example 1 | 2 |
| Comparative Example 1 (PICOLYTE) | 7 |
| Comparative Example 2 (CoolPrep) | 53 |

As shown in the above results, the percentage of non-recommendation was quite high (53%) in case of Comparative Example 2.

Meanwhile, Comparative Example 1 showed a relatively lower percentage of non-recommendation with a rate of 7%, which is slightly higher than that of Example 1. This may be viewed as being associated with its large volume of ingestion amounting to 2.3 L.

Need for Improvement

In a questionnaire, the subjects were asked if the bowel cleansing agent they used needs improvement, and the percentages of subjects who answered affirmatively are shown in Table 10.

TABLE 10

| Sample | Need for improvement (%) |
| --- | --- |
| Example 1 | 5 |
| Comparative Example 1 (PICOLYTE) | 7 |
| Comparative Example 2 (CoolPrep) | 58 |

From the above results, it can be seen that Example 1 shows the highest satisfaction as the percentage of subjects who saw the need for improvement is the lowest. In comparison, 7% of the subjects saw the need for improvement in Comparative Example 1 and 58% of the subjects saw the need for improvement in Comparative Example 2.

Patient Preferences for Example 1 and Other Bowel Cleansing Agents

Among the subjects who were given the bowel cleansing composition of Example 1, 89 subjects who had previously experienced colon preparation were asked if the ease of administration was enhanced compared to their previous colon preparation experiences. The results are shown in Table 11.

TABLE 11

| Relative Ease of Use | | Percentage of subjects having experience with other bowel cleansing agents (%) |
| --- | --- | --- |
| Easier | Much easier | 57.4 |
| | Slightly easier | 21.3 |
| | Comparable | 21.3 |
| | More difficult | 0 |

As can be seen from the above results, 78.7% of the subjects who had experienced other bowel cleansing agents replied that consumption of the bowel cleansing composition of Example 1 was easier, while none of the subjects found it more difficult. These results allows for an indirect comparison between the existing bowel cleansing agents in Comparative Examples 1 and 2 and the preparation of Example 1, which shows a significantly favorable preference for the preparation of Example 1.

Experimental Example 4: Safety (In Vivo Test)

The safety of each bowel cleansing agent was assessed by conducting blood tests for the blood ascorbic acid concentration, and blood chemistry.

Colonic Gas Measurement

With respect to the production of combustible gases, further to the above in vitro test showing the safety of the bowel cleansing composition of the present invention, for each of the 10 subjects who used the bowel cleansing composition of Example 1, actual colonic gas collected during their colonoscopy was analyzed. The results showed that the methane concentration was 0.1~0.3 vol % and the hydrogen concentration was 1~7 ppm, directly demonstrating that the concentrations of these gases are in no way close to their minimum explosive concentrations, i.e., 5% and 4,000 ppm, respectively.

Blood Ascorbic Acid Concentration

Following the consumption of the bowel cleansing compositions, blood samples were taken from subjects just before their colonoscopy, and the blood ascorbic acid concentrations were measured at the SCL (Seoul Medical Science Institute), a testing institution equipped with apparatus for measuring ascorbic acid blood levels. The resulting average values are listed in Table 12.

TABLE 12

| Sample | Average blood ascorbic acid concentration (reference range: 2-20 μg/mL) |
| --- | --- |
| Example 1 | 32.4 |
| Comparative Example 1 (PICOLYTE) | 6.9 |
| Comparative Example 2 (CoolPrep) | 30.4 |

The reference range for blood ascorbic acid concentration is 2-20 μg/mL. It can be expected that the blood ascorbic acid concentration is transiently elevated above the reference range with Comparative Example 3 where 21.2 g of ascorbic acid is mixed in the ingested liquid as well as with Example 1 containing 25 g of ascorbic acid compounds. However, since ascorbic acid is water soluble, blood ascorbic acid exceeding the reference value is directly excreted via the kidney to reduce the blood concentration to normal.

In addition, the U.S. National Cancer Institute has officially confirmed that high dose ascorbic acid is not harmful to the human body (http://www.cancer.gov/cancertopics/pdq/cam/highdosevitaminc/healthprofessional/page1/All-Pages).

Since the 1970s, many studies have been conducted to determine if an intravenous injection of high dose ascorbic acid has therapeutic effects on various cancers. While there is no consensus on its therapeutic effect, it was confirmed along the way that except for people with G6PD deficiency, renal disorders or urolithiasis, up to 1.5 g/kg of ascorbic acid can be safely administered intravenously to a healthy person <"Vitamin C pharmacokinetics: implications for oral and intravenous use", Padayatty S J, Sun H, Wang Y, et al., *Ann Intern Med* 140 (7), 533-7, 2004; "Phase I clinical trial of i.v. ascorbic acid in advanced malignancy", Hoffer L J, Levine M, Assouline S, et al., *Ann Oncol* 19 (11), 1969-74, 2008>.

It was also reported in a phase I clinical study conducted in 2013 that ascorbic acid 15 g given intravenously over 30 minutes twice weekly for four weeks elevated the blood ascorbic acid level to at least 350 mg/dL (3,500 μg/mL), yet was very well tolerated and caused no severe adverse effects <"Pharmacological ascorbate with gemcitabine for the control of metastatic and node-positive pancreatic cancer (PACMAN): results from a phase I clinical trial", Welsh J L, Wagner B A, van't Erve T J, et al., *Cancer Chemother Pharmacol* 71 (3), 765-75, 2013>

The above information is found in official resources published on the website of the U.S. National Cancer Institute, confirming that high blood ascorbic acid concentration causes no harm to human health. In addition, the above-referenced ascorbic acid blood concentration of 3,500 μg/mL is almost 175 times the upper limit of its reference range and 108 times as high as 32.4 μg/mL, the average blood ascorbic acid concentration observed after using the bowel cleansing composition of Example 1. That is, it can be seen that the elevation of ascorbic acid concentration after consuming the bowel cleansing composition of Example 1 does no harm to human health.

It is believed that for these reasons, MoviPrep® was able to be approved by the U.S. FDA as a bowel cleansing agent without difficulty despite having the same composition as CoolPrep (used in Comparative Example 2), which has been shown to cause transient elevation of the blood ascorbic acid level.

Other Blood Chemistry Test

As other blood chemistry tests, magnesium concentrations, electrolyte concentrations, concentrations of blood urea nitrogen (BUN) and creatinine, which are indicators of kidney functions, as well as liver enzymes AST (GPT) and ALT (GPT) reflecting liver damage were measured and the results are shown in Tables 13-16. Blood was collected right before the colonoscopy and measurements were taken at the Department of Laboratory Medicine at Joyful Hospital following the usual protocol.

TABLE 13

| Samples | Mg (reference range: 1.58-2.55 mg/dL) |
| --- | --- |
| Example 1 | 2.1 |
| Comparative Example 1 (PICOLYTE) | 2.5 |
| Comparative Example 2 (CoolPrep) | 2.2 |

TABLE 14

| Samples | Na (reference range: 135-145 mmol/L) | K (reference range: 3.5-5.5 mmol/L) | Cl (reference range: 98-110 mmol/L) |
| --- | --- | --- | --- |
| Example 1 | 140.7 | 4.5 | 104.5 |
| Comparative Example 1 (PICOLYTE) | 140.3 | 4.0 | 102.2 |
| Comparative Example 2 (CoolPrep) | 144.9 | 4.6 | 108.2 |

TABLE 15

| Samples | BUN (reference range: 5-23 mg/dL) | Creatinine (reference range: 0.5-1.2 mg/dL) |
| --- | --- | --- |
| Example 1 | 10.8 | 0.7 |
| Comparative Example 1 (PICOLYTE) | 11.8 | 0.8 |
| Comparative Example 2 (CoolPrep) | 12.4 | 0.8 |

TABLE 16

| Samples | AST(GOT) (reference range: 0-32 IU/L) | ALT(GPT) (reference range: 0-31 IU/L) |
| --- | --- | --- |
| Example 1 | 24.4 | 24.5 |
| Comparative Example 1 (PICOLYTE) | 24.6 | 25.7 |
| Comparative Example 2 (CoolPrep) | 28 | 24.3 |

As can be seen from the above results, except for the fact that magnesium concentration was 2.5 mg/dL which is close to its upper limit (reference range 1.58~2.55 mg/dL) in subjects receiving the bowel cleansing composition of Comparative Example 1, no abnormalities were observed in the results for the concentrations of electrolytes, kidney function indicators BUN and creatinine, and liver enzymes AST and ALT, for all of the bowel cleansing agents.

The reason the magnesium blood concentration was elevated close to its upper limit in patients receiving the bowel cleansing composition of Comparative Example 1 is because a large amount of magnesium oxide (10.5 g) is included in PICOLYTE.

To sum up, it has been shown that like other bowel cleansing agents, the bowel cleansing composition of Example 1 is a safe pharmaceutical preparation which does not cause hematochemical abnormalities.

INDUSTRIAL APPLICABILITY

By combining specific concentrations of a sugar alcohol, ascorbic acid, and picosulfate, the bowel cleansing composition according to the present invention displays superior cleansing efficacy as well as improved taste compared to existing bowel cleansing agents. The bowel cleansing composition according to the present invention also greatly enhances the ease of administration and compliance by significantly reducing the volume of ingestion. In addition, the bowel cleansing composition according to the present invention improves patient discomfort by minimizing discomforts during its consumption such as nausea, abdominal pain and vomiting. By incorporating bicarbonates such as sodium bicarbonate, potassium bicarbonate, etc., it can prevent electrolyte abnormalities such as hyponatremia, hypopotassemia, etc., which can occur with the existing picosulfate-containing bowel cleansing agents. Since the bowel cleansing composition of the present invention does not contain any magnesium, it can be safely used in patients with renal disorders with no severe side effects.

What is claimed:

1. A bowel cleansing powder composition consisting of:
   as a first cleansing ingredient, at least one sugar alcohol selected from xylitol, sorbitol, glycerol, erythritol, threitol, arabitol, ribitol, mannitol, galactitol, fucitol, iditol, inositol, volemitol, isomalt, maltitol, lactitol, maltotriitol, maltotetraitol, and polyglycitol; as a second cleansing ingredient, ascorbic acid or a mixture of ascorbic acid and a salt of ascorbic acid; and as a third cleansing ingredient picosulfate;
   wherein said first cleansing ingredient is in an amount so that its concentration is 10 g/L to 500 g/L based on the total composition when the bowel cleansing powder composition is mixed with an aqueous solvent,
   said second ingredient is in an amount so that its concentration is 15 g/L to 500 g/L based on the total composition when the bowel cleansing powder composition is mixed with an aqueous solvent,
   said third ingredient is in an amount so that its concentration is 1 mg/L to 100 mg/L based on the total composition when the bowel cleansing powder composition is mixed with an aqueous solvent.

2. The bowel cleansing powder composition of claim 1, wherein said first cleansing ingredient is xylitol.

3. The bowel cleansing powder composition of claim 1, wherein said first cleansing ingredient is sorbitol.

4. The bowel cleansing powder composition of claim 1, wherein said first cleansing ingredient is a mixture of xylitol and sorbitol.

5. The bowel cleansing powder composition of claim 1, wherein, when said second cleansing ingredient is a mixture of ascorbic acid and a salt of ascorbic acid, the mass ratio of ascorbic acid to the salt of ascorbic acid ranges from 99:1 to 60:40.

6. The bowel cleansing powder composition of claim 1, which is mixed with 0.1 L to 1.5 L of an aqueous solvent before ingestion.

7. The bowel cleansing powder preparation composition of claim 6, wherein said aqueous solvent is carbonated water.

8. The bowel cleansing powder preparation composition of claim 1, wherein said first cleansing ingredient is in an amount so that its concentration is 50 g/L to 150 g/L based on the total composition when the bowel cleansing powder composition is mixed with an aqueous solvent.

9. The bowel cleansing powder preparation composition of claim 1, wherein said second cleansing ingredient is in an amount so that its concentration is 30 g/L to 200 g/L based on the total composition when the bowel cleansing powder composition is mixed with an aqueous solvent.

10. The bowel cleansing powder preparation composition of claim 1, wherein said third cleansing ingredient is in an amount so that its concentration is 10 mg/L to 80 mg/L based on the total composition when the bowel cleansing powder composition is mixed with an aqueous solvent.

11. The bowel cleansing powder composition of claim 6, wherein the volume of said aqueous solvent is 0.3 L to 0.7 L.

12. A bowel cleansing composition package which is a two-part product consisting of (i) a package containing a highly concentrated solution formulated by mixing the bowel cleansing powder composition of claim 1 in 0.05 L to 0.2 L of total volume of an aqueous solvent and (ii) a separate package containing the remaining amount of the aqueous solvent that is its total volume minus the volume used in formulating the highly concentrated solution,
wherein the total volume of the aqueous solvent is 0.1 L to 1.5 L.

13. The bowel cleansing powder composition of claim 6, wherein said aqueous solvent is water, carbonated water, alkaline ionized water or a beverage.

14. The bowel cleansing powder composition of claim 1 consisting of:
as a first cleansing ingredient, at least one sugar alcohol which is sorbitol;
as a second cleansing ingredient, ascorbic acid;
and as a third cleansing ingredient picosulfate;
wherein said first cleansing ingredient is in an amount so that its concentration is 10 g/L to 500 g/L based on the total composition when the bowel cleansing powder composition is mixed with an aqueous solvent,
said second ingredient is in an amount so that its concentration is 30 g/L to 200 g/L based on the total composition when the bowel cleansing powder composition is mixed with an aqueous solvent,
said third ingredient is in an amount so that its concentration is 1 mg/L to 100 mg/L based on the total composition when the bowel cleansing powder composition is mixed with an aqueous solvent, and wherein the total aqueous solution volume of the bowel cleansing composition dissolved in an aqueous solvent is not greater than 1.5 L.

\* \* \* \* \*